(12) United States Patent
Chen et al.

(10) Patent No.: US 12,356,855 B2
(45) Date of Patent: Jul. 8, 2025

(54) ORGANIC ELECTROLUMINESCENCE DEVICE, DISPLAY PANEL, DISPLAY DEVICE, AND LIGHT EMITTING DEVICE

(71) Applicant: BOE TECHNOLOGY GROUP CO., LTD., Beijing (CN)

(72) Inventors: Xueqin Chen, Beijing (CN); Yang Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 905 days.

(21) Appl. No.: 17/611,676

(22) PCT Filed: Dec. 25, 2020

(86) PCT No.: PCT/CN2020/139629
§ 371 (c)(1),
(2) Date: Nov. 16, 2021

(87) PCT Pub. No.: WO2022/134074
PCT Pub. Date: Jun. 30, 2022

(65) Prior Publication Data
US 2022/0416175 A1 Dec. 29, 2022

(51) Int. Cl.
*H10K 50/18* (2023.01)
*H10K 85/60* (2023.01)
*H10K 50/11* (2023.01)
*H10K 101/10* (2023.01)

(52) U.S. Cl.
CPC ....... *H10K 85/657* (2023.02); *H10K 85/6572* (2023.02); *H10K 85/6574* (2023.02); *H10K 50/11* (2023.02); *H10K 50/18* (2023.02); *H10K 50/181* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 10,763,448 B2* | 9/2020 | Jiao | H10K 50/16 |
| 2015/0060808 A1 | 3/2015 | Kim | |
| 2015/0318510 A1* | 11/2015 | Ito | H10K 85/654 |
| | | | 257/40 |
| 2016/0225992 A1* | 8/2016 | Ito | C09B 57/02 |
| 2016/0308138 A1* | 10/2016 | Kim | H10K 50/11 |
| 2017/0005276 A1* | 1/2017 | Kim | C07D 403/14 |
| 2017/0117485 A1* | 4/2017 | Cho | C07D 405/14 |
| 2017/0117486 A1* | 4/2017 | Cho | H10K 85/657 |
| 2019/0074451 A1* | 3/2019 | Lee | C07D 405/14 |
| 2019/0097140 A1* | 3/2019 | Kim | C07D 209/86 |
| 2021/0119168 A1* | 4/2021 | Choi | H10K 85/6574 |

FOREIGN PATENT DOCUMENTS

| | | | |
|---|---|---|---|
| CN | 106536527 A | 3/2017 | |
| CN | 107275496 A | 10/2017 | |
| CN | 107619412 A | 1/2018 | |
| CN | 108218853 A * | 6/2018 | .......... C07D 401/14 |
| CN | 110416256 A | 11/2019 | |
| CN | 111349103 A | 6/2020 | |
| CN | 111499646 A | 8/2020 | |
| CN | 111635324 A | 9/2020 | |
| CN | 112028902 A | 12/2020 | |
| JP | 2015019019 A | 1/2015 | |
| KR | 20180008279 A | 1/2018 | |
| KR | 20180138422 A | 12/2018 | |
| KR | 20190010499 A | 1/2019 | |
| KR | 101959047 B1 | 3/2019 | |
| KR | 101985588 B1 | 6/2019 | |
| KR | 102080289 B1 | 2/2020 | |
| TW | 201412746 A | 4/2014 | |
| WO | 2013179645 A1 | 12/2013 | |
| WO | 2014057659 A1 | 4/2014 | |

OTHER PUBLICATIONS

Written Opinion for PCT Patent Application No. PCT/CN2020/139629 mailed Sep. 29, 2021.

* cited by examiner

*Primary Examiner* — Robert S Loewe
(74) *Attorney, Agent, or Firm* — Perilla Knox & Hildebrandt LLP; Kenneth A. Knox (57) ABSTRACT

An organic electroluminescent device, a display panel, a display device, and a light emitting device are described. The organic electroluminescent device includes an anode, an electron blocking layer, a buffer layer, an organic light emitting layer, and a cathode that are sequentially stacked. The thickness of the buffer layer is in a range from 1 nm to 100 nm. The material of the buffer layer comprises a compound shown in a first chemical formula as below:

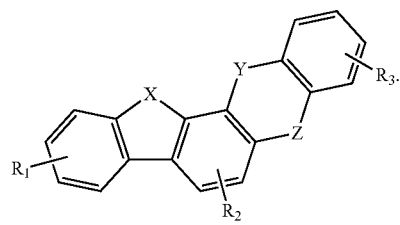

The organic electroluminescence device can improve the life of the device.

18 Claims, 2 Drawing Sheets

ORGANIC ELECTROLUMINESCENCE DEVICE, DISPLAY PANEL, DISPLAY DEVICE, AND LIGHT EMITTING DEVICE

CROSS-REFERENCE TO RELATED APPLICATION

The present application is a national phase application under 35 U.S.C. § 371 of International Application No. PCT/CN2020/139629 filed on Dec. 25, 2020, the entire disclosure of which is incorporated herein as a part of the present application for all purposes.

TECHNICAL FIELD

The present disclosure relates to the field of display technology and, in particular, to an organic electroluminescent device, a display panel, a display device, and a light emitting device.

BACKGROUND

Organic electroluminescence device (also referred to as OLED) display panels have advantages such as high color gamut, lightness and thinness, flexibility, etc., and are more and more widely used in the display field. In the relevant art, the highest occupied molecular orbital (HOMO) energy level of the host material of the organic light emitting layer is relatively deep. An electron blocking layer material has not yet been developed which can match the highest occupied molecular orbital energy level of the host material and meet the requirements of OLED in other properties. This leads to a relatively large difference in the highest occupied molecular orbital energy level between the electron blocking layer and the host material, thus reducing the efficiency of the electron blocking layer in injecting holes into the organic light emitting layer.

It should be noted that the information disclosed in the background art section above is only used to enhance the understanding of the background of the present disclosure, and therefore may include information that does not constitute the prior art known to those of ordinary skill in the art.

SUMMARY

According to an aspect of the present disclosure, there is provided an organic electroluminescent device, including an anode, an electron blocking layer, a buffer layer, an organic light emitting layer, and a cathode that are sequentially stacked. The thickness of the buffer layer is in the range of 1-100 nm. The material of the buffer layer includes the compound shown in a first chemical formula as below:

In the first chemical formula, X is O or S; one of Y and Z is N ($R_4$) and the other of Y and Z is a single bond; $R_1$, $R_2$, and $R_3$ are each independently selected from: hydrogen, deuterium, fluorine, cyano, halogen, alkyl group with 1 to 6 carbon atoms, cycloalkyl group with 5 to 10 carbon atoms, substituted or unsubstituted aryl group with 6 to 30 carbon atoms in total, and substituted or unsubstituted heteroaryl group with 4 to 30 carbon atoms in total; and at least one of $R_1$, $R_2$, and $R_3$ is selected from a group shown in a second chemical formula as below:

$R_4$ is selected from: alkyl group with 1 to 6 carbon atoms, cycloalkyl group with 5 to 10 carbon atoms, aryl group with 6 to 30 carbon atoms, and heteroaryl group with 4 to 30 carbon atoms.

In an exemplary embodiment of the present disclosure, $R_1$, $R_2$, and $R_3$ are each independently selected from: hydrogen, and substituted or unsubstituted group Ar. The unsubstituted group Ar is selected from the following groups:

The substituted group Ar is a new group formed by substituting the above-mentioned unsubstituted group Ar with one or more substituent groups. Each substituent group on the substituted group Ar is independently selected from: deuterium, fluorine, chlorine, cyano, alkyl group with 1-6 carbon atoms, and cycloalkyl group with 3-10 carbon atoms. In a case that the substituted group Ar has more than one substituent group, each substituent group is the same or different.

In an exemplary embodiment of the present disclosure, the buffer layer includes one or both of:
a compound shown in a third chemical formula as below:

and
a compound shown in a fourth chemical formula as below:

In an exemplary embodiment of the present disclosure, the organic light emitting layer is an organic light emitting layer for emitting blue light.

In an exemplary embodiment of the present disclosure, the thickness of the buffer layer is 0.05 to 0.20 times the thickness of the organic light emitting layer.

In an exemplary embodiment of the present disclosure, the organic light emitting layer includes a host material and a guest material mixed with each other. The lowest unoccupied molecular orbital energy level of the host material is lower than the lowest unoccupied molecular orbital energy level of the material of the buffer layer by at least 0.15 eV.

In an exemplary embodiment of the present disclosure, the lowest unoccupied molecular orbital energy level of the host material is in the range from −2.75 eV to −3.15 eV.

In an exemplary embodiment of the present disclosure, the lowest unoccupied molecular orbital energy level of the material of the buffer layer is in a range from −2.25 eV to −2.65 eV.

In an exemplary embodiment of the present disclosure, the highest occupied molecular orbital energy level of the material of the buffer layer is higher than the highest occupied molecular orbital energy level of the host material, and the highest occupied molecular orbital energy level of the material of the buffer layer is in the range from −5.4 eV to −6 eV.

In an exemplary embodiment of the present disclosure, the highest occupied molecular orbital energy level of the material of the buffer layer is in the range from −5.5 eV to −5.8 eV.

In an exemplary embodiment of the present disclosure, the highest occupied molecular orbital energy level of the host material is in the range from −5.8 eV to −6.2 eV.

In an exemplary embodiment of the present disclosure, the highest occupied molecular orbital energy level of the material of the electron blocking layer is in the range from −5.25 eV to −5.65 eV, and is higher than the highest occupied molecular orbit energy level of the material of the buffer layer.

In an exemplary embodiment of the present disclosure, the hole mobility of the host material is less than the electron mobility of the host material.

In an exemplary embodiment of the present disclosure, the excited triplet energy level of the material of the buffer layer is not less than 2.5 eV; and the host material is a thermally activated delayed fluorescent material.

In an exemplary embodiment of the present disclosure, the material of the buffer layer is composed of a compound shown in the first chemical formula.

In an exemplary embodiment of the present disclosure, the thickness of the buffer layer is in a range from 3 nm to 20 nm.

According to another aspect of the present disclosure, there is provided a display panel, including the above-mentioned organic electroluminescent device.

According to another aspect of the present disclosure, there is provided a display device, including the above-mentioned display panel.

According to another aspect of the present disclosure, there is provided a light emitting device, including the above-mentioned organic electroluminescent device.

It should be understood that the above general description and the following detailed description are only exemplary and explanatory, and cannot limit the present disclosure.

BRIEF DESCRIPTION OF THE DRAWINGS

The drawings herein are incorporated into the specification and constitute a part of the specification, show embodiments in accordance with the present disclosure, and are used together with the specification to explain the principle of the present disclosure. Understandably, the drawings in the following description are only some embodiments of the present disclosure. For those of ordinary skill in the art, other drawings can be obtained based on these drawings without creative work.

DETAILED DESCRIPTION

Example embodiments will now be described more fully with reference to the accompanying drawings. However, the example embodiments can be implemented in various forms, and should not be construed as being limited to the embodiments set forth herein. On the contrary, these embodiments are provided so that the present disclosure will be comprehensive and complete, and fully convey the concept of the example embodiments to those skilled in the art. The same reference numerals in the figures indicate the same or similar structures, and thus their detailed descriptions will be omitted. In addition, the drawings are only schematic illustrations of the present disclosure, and are not necessarily drawn to scale.

In the related art, an organic electroluminescent device may include a hole transport layer, an electron blocking layer, and an organic light emitting layer that are stacked over each other. The organic light emitting layer may be a mixed film layer of a host material and a guest material, wherein the host material is used to transport electrons and holes, and transfer excitons generated by the recombination of electrons and holes to the guest material, so that the guest material emits light. The highest occupied molecular orbital (HOMO) energy level of the host material is generally relatively deep, and the HOMO energy level of the electron blocking layer is higher than the HOMO energy level of the host material, so as to improve the efficiency of the hole transport layer in injecting holes into the organic light emitting layer. However, in the related art, no electron blocking layer material has been found that has a relatively deep HOMO energy level and meets the requirements in other characteristics such as electrochemical stability and hole mobility. This makes the energy level difference between the HOMO energy level of the currently used electron blocking layer material and the HOMO energy level of the host material to be relatively large, causing holes to accumulate at the interface between the electron blocking layer and the organic light emitting layer, and restricting the further improvement of the efficiency of hole injection into the organic light emitting layer.

The reference numerals used in the figures are as follows: 100, anode; 200, cathode; 301, hole injection layer; 302, hole transport layer; 303, electron blocking layer; 304, buffer layer; 305, organic light emitting layer; 306, hole blocking layer; 307, electron transport layer; and 308, electron injection layer.

Figure 1:
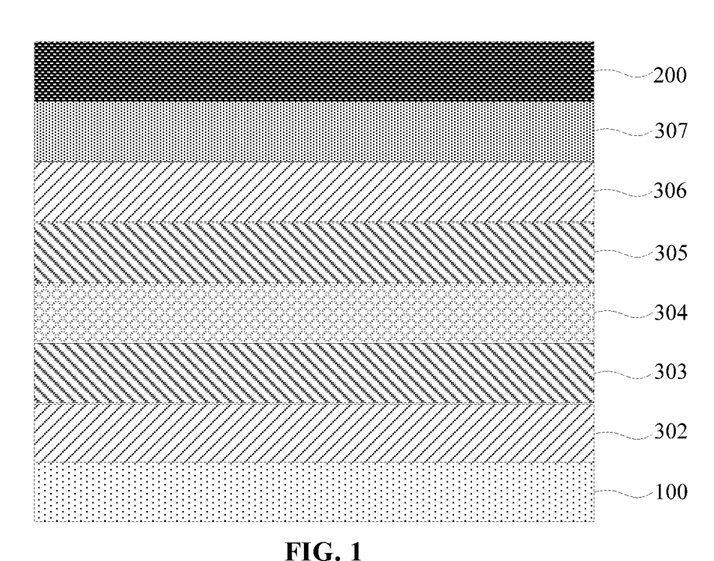
FIG. 1 is a schematic structural diagram of an organic electroluminescent device in an embodiment of the disclosure.

The present disclosure provides an organic electroluminescent device. Referring to FIG. 1, the organic electroluminescent device includes an anode 100, a hole transport layer 302, an electron blocking layer 303, a buffer layer 304, an organic light emitting layer 305, and a cathode 200 which are sequentially stacked. The thickness of the buffer layer 304 is in the range from 1 nm to 100 nm.

The material of the buffer layer 304 includes the compound shown in a first chemical formula as below:

In the first chemical formula, X is O or S; one of Y and Z is N ($R_4$) and the other of Y and Z a single bond; $R_1$, $R_2$ and $R_3$ are each independently selected from: hydrogen, deuterium, fluorine, cyano, halogen, alkyl group with 1 to 6 carbon atoms, cycloalkyl group with 5 to 10 carbon atoms, and substituted or unsubstituted aryl group with 6 to 30 carbon atoms in total, and substituted or unsubstituted heteroaryl group with 4 to 30 carbon atoms in total; and at least one of $R_1$, $R_2$, and $R_3$ is selected from the group shown in the second chemical formula as below:

Besides, $R_4$ is selected from: alkyl group with 1 to 6 carbon atoms, cycloalkyl group with 5 to 10 carbon atoms, aryl group with 6 to 30 carbon atoms, and heteroaryl group with 4 to 30 carbon atoms.

In the organic electroluminescent device provided by the present disclosure, the structure of the buffer layer 304 is as shown in the first chemical formula. The core of the compound shown in the first chemical formula has a larger and rigid conjugate plane, and thus has a deeper HOMO energy level. The compound shown in the first chemical formula also has 9-carbazole attached to the core, which 9-carbazole is shown in the second chemical formula. This can improve the hole mobility of the compound shown in the first chemical formula and appropriately increase its HOMO energy level, thereby preventing its HOMO energy level from being too low. In this way, the HOMO energy level of the buffer layer 304 may be located between the HOMO energy level of the electron blocking layer 303 and the HOMO energy level of the host material of the organic light emitting layer 305. Adjacent ones among the electron blocking layer 303, the buffer layer 304, and the organic light emitting layer 305 have a small difference in the HOMO energy level therebetween. This reduces the energy barrier for hole injection from the previous film layer to the next film layer, thereby increasing the hole injection efficiency. In order to alleviate the defect of insufficient hole mobility of the compound shown by the first chemical formula, and to prevent the insufficient hole mobility of the buffer layer 304 from severely reducing the efficiency of injecting holes into the organic light emitting layer 305, the thickness of the buffer layer 304 is controlled within the range from 1 nm to 100 nm. In this way, the buffer layer 304 helps to improve the efficiency of injecting holes into the organic light emitting layer 305 as a whole. This can increase the electron-hole recombination rate in the organic light emitting layer 305, and reduce the electron entry into the buffer layer 304 and the electron blocking layer 303. Thus, the impact of the electron flow on the buffer layer 304 and the electron blocking layer 303 is further reduced, and the damage of materials of the buffer layer 304 and the electron blocking layer 303 by the electron is reduced, thereby increasing the life of the organic electroluminescent device. Additionally, the compound represented by the first chemical formula does not contain a triarylamine structure, which makes it have a relatively suitable electron cloud density and a sufficiently high resistance to electrons. This can prevent the organic light emitting layer 305 from injecting electrons to cause its structural damage, and improve its electrochemical stability.

In the organic electroluminescent device of the present disclosure, the compound shown in the first chemical formula as used in the buffer layer 304 can meet the requirements of the organic electroluminescent device in terms of HOMO energy level and electronic tolerance. Besides, by providing the buffer layer 304 with a small thickness, the effect of insufficient hole mobility of the compound represented by the first chemical formula is reduced. Therefore, although a material may not be obtained with various properties such as having sufficient hole mobility, having sufficiently deep HOMO energy level, matching the HOMO energy level of the host material of the organic light emitting layer 305, and having sufficiently high tolerance to electrons, the organic electroluminescent device of the present disclosure makes balance among the HOMO energy level, electron tolerance, hole mobility, thickness, and other aspects of the buffer layer 304, and finally enables the buffer layer 304 to improve the life of the organic electroluminescence device.

Optionally, $R_1$, $R_2$, and $R_3$ are each independently selected from: hydrogen, and substituted or unsubstituted group Ar. The unsubstituted group Ar is selected from the following groups:

The substituted group Ar is a new group formed by substituting the above-mentioned unsubstituted group Ar with one or more substituent groups. Each substituent group on the substituted group Ar is independently selected from: deuterium, fluorine, chlorine, cyano, alkyl group with 1 to 6 carbon atoms, and cycloalkyl group with 3 to 10 carbon atoms. When the substituted group Ar has more than one substituent group, each substituent group is the same or different.

In this way, each of the substituent groups shown in the first chemical formula does not contain a diarylamine group. This can prevent the diarylamine group from causing too much electron cloud density on the compound shown in the first chemical formula and avoid the compound shown in the first chemical formula to have a reduced resistance to electrons. Referring to FIG. 1, the buffer layer 304 is in direct contact with the organic light emitting layer 305, and electrons in the organic light emitting layer 305 may cross the energy barrier, thereby entering the buffer layer 304 and even the electron blocking layer 303. If the compound represented by the first chemical formula has insufficient resistance to electrons, it will be easily destroyed under the impact of the electron flow, which will result in a decrease in the life of the organic electroluminescent device. Of course, it is understood that since the compound of the present disclosure does not greatly increase its electron cloud density through substituent groups, and especially does not form a triarylamine structure, the hole mobility thereof is affected. This is the balance among the HOMO energy level, electrochemical stability and hole mobility of the compound shown in the first chemical formula of the present disclosure.

In an embodiment of the present disclosure, the buffer layer 304 includes a compound shown in a third chemical formula as below:

or a compound shown in a fourth chemical formula as below:

In an embodiment of the present disclosure, the material of the buffer layer 304 is composed of the compound shown in the first chemical formula.

In an embodiment of the present disclosure, the organic light emitting layer 305 is a blue organic light emitting layer, that is, an organic light emitting layer 305 for emitting blue light, and in particular, an organic light emitting layer 305 for emitting blue fluorescence. Compared with the organic light emitting layer 305 of other colors, the HOMO energy level of the host material in the blue organic light emitting layer 305 is deeper (lower). Thus, it is more difficult to obtain a material for the buffer layer 304 that matches the HOMO energy level of the host material in the blue organic light emitting layer 305 and has other properties that fully meet the requirements. Especially, in some display panels, the material of the hole transport layer 302 of the organic electroluminescent devices used to emit different colors can be completely the same, so as to achieve the purpose of simplifying the process. The host material of the organic light emitting layer 305 of the organic electroluminescent device of different colors has different requirements for the HOMO energy level. The HOMO energy level of the host material in the blue organic light emitting layer 305 is deeper. This makes the HOMO energy level difference between the host material of the blue organic light emitting layer 305 and the hole transport layer 302 to be larger, rendering it more difficult to obtain a suitable material for the electron blocking layer 303. In addition, since holes are difficult to be injected into the organic light emitting layer 305, electrons in the organic light emitting layer 305 are easier to jump to the electron blocking layer. This easily causes the material of the electron blocking layer to be destroyed by the electrons, which in turn leads to a reduced life of the organic electroluminescent device.

The material of the buffer layer 304 of the present disclosure makes balance among the HOMO energy level, electrochemical stability, hole mobility, and thickness, so as to improve the performance of the blue organic electroluminescent device as a whole, especially realizing life improvement.

Figure 3:
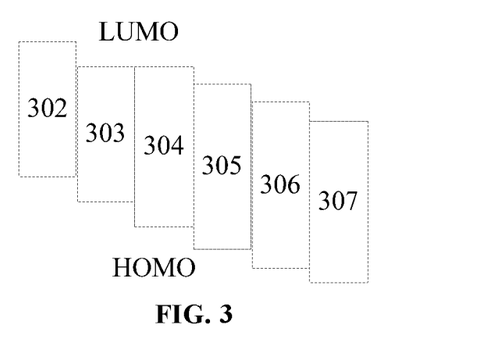
FIG. 3 is a schematic energy level diagram of part of the film layers of an organic electroluminescent device in an embodiment of the present disclosure.

Optionally, referring to FIG. 3, the HOMO energy level of the material of the buffer layer 304 is higher than the HOMO energy level of the host material. In an embodiment of the present disclosure, the HOMO energy level of the material of the buffer layer 304 is in the range from −5.4 eV to −6 eV. Further, the HOMO energy level of the material of the buffer layer 304 is in the range from −5.5 eV to −5.8 eV.

In another embodiment of the present disclosure, the HOMO energy level of the host material is in the range from −5.8 eV to −6.2 eV.

Optionally, referring to FIG. 3, the HOMO energy level of the material of the buffer layer 304 is lower than the HOMO energy level of the material of the electron blocking layer 303. In an embodiment of the present disclosure, the HOMO energy level of the material of the electron blocking layer 303 is in the range from −5.25 eV to −5.65 eV.

Optionally, referring to FIG. 3, the lowest unoccupied molecular orbital (LUMO) energy level of the host material of the organic light emitting layer 305 is lower than the LUMO energy level of the material of the buffer layer 304 by at least 0.15 eV. The LUMO energy level of the buffer layer 304 may be higher than the LUMO energy level of the host material of the light emitting layer, so that the buffer layer 304 can achieve a certain electron blocking effect. In an embodiment of the present disclosure, the LUMO energy level of the host material is in the range from −2.75 eV to −3.15 eV. In another embodiment of the present disclosure, the LUMO energy level of the material of the buffer layer 304 is low in a range from −2.25 eV to −2.65 eV.

Optionally, the LUMO energy level of the material of the buffer layer 304 may be close to the LUMO energy level of the electron blocking layer 303, and the energy level difference between the two may not be greater than 0.3 eV. In an embodiment of the present disclosure, the LUMO energy level of the electron blocking layer 303 is in the range from −2.2 eV to −2.6 eV.

Optionally, in the host material, the hole mobility is less than the electron mobility. In this way, in the organic light emitting layer 305, the recombination center of holes and electrons is close to the side of the buffer layer 304. This requires that the buffer layer 304 has a good barrier effect on electrons and can withstand the impact of the electron flow. The compound represented by the first chemical formula according to the present disclosure can meet the above requirements. On the other hand, since the recombination center of holes and electrons is close to the side of the buffer layer 304, thinning the organic light emitting layer 305 will not cause a significant decrease in the hole-electron recombination rate, and will not cause the light emission efficiency of the organic electroluminescent device to decline. In addition, since the host material has a relatively fast transfer rate of electrons, if the buffer layer 304 is not provided, the electron flow is easy to impact the electron blocking layer 303, which will cause the material of the electron blocking layer 303 to be damaged under the impact of the electron flow, thereby reducing the life of the organic electroluminescent device. In the present disclosure, the buffer layer 304 can block and buffer electrons to prevent electron flow from impacting the electron blocking layer 303, thereby increasing the material life of the electron blocking layer 303 and increasing the life of the organic electroluminescent device.

Optionally, the host material is a thermally activated delayed fluorescent material, so that triplet excitons can be converted into singlet excitons, and the guest material can emit fluorescence using the singlet excitons. In this way, the organic electroluminescence device can simultaneously utilize triplet excitons and singlet excitons, thus having high internal quantum efficiency. Further, the excited triplet energy level of the material of the buffer layer 304 is not less than 2.5 eV. In this way, the buffer layer 304 can block the diffusion of triplet excitons and confine the triplet excitons in the organic light emitting layer 305 as much as possible, thus improving the internal quantum efficiency of the organic electroluminescent devices. In an embodiment of the present disclosure, the excited triplet energy level of the material of the buffer layer 304 is not lower than 2.6 eV.

Referring to FIG. 1, the organic electroluminescent device provided by the present disclosure includes a cathode 200 and an anode 100 arranged oppositely. The material of the anode 100 can be selected from conductive materials with a large work function, so as to facilitate hole injection into the organic layer between the cathode 200 and the anode 100. Exemplarily, the material of the anode 100 can be selected from metals or alloys, such as nickel, platinum, vanadium, chromium, copper, zinc, and gold or their alloys. It can also be selected from metal oxides, such as zinc oxide, indium oxide, indium tin oxide (ITO), and indium zinc oxide (IZO), etc. It can also be selected from the combination of metal oxides and metals. For example, it can be selected from ZnO:Al or SnO2: Sb, etc. It can also be selected from conductive polymers, for example, poly(3-methylthiophene), poly[3,4-(ethylidene-1,2-dioxy)thiophene] (PEDT), polypyrrole, polyaniline, and the like.

The material of the cathode 200 may be selected from materials having a small work function, so as to facilitate electron injection into the organic layer between the cathode 200 and the anode 100. Exemplarily, the material of the cathode 200 may be selected from metals or alloys, for example, selected from magnesium, calcium, sodium, potassium, titanium, indium, yttrium, lithium, gadolinium, aluminum, silver, tin, and lead, or their alloys. The present disclosure does not specifically limit the materials of the cathode 200 and the anode 100.

It can be understood that at least one of the cathode 200 and the anode 100 is a transparent electrode to ensure that the organic electroluminescent device emits light outward.

The organic electroluminescent device may include a hole transport layer 302 provided between the electron blocking layer 303 and the anode 100. The hole transport layer 302 is used to transport holes from the anode 100 to the electron blocking layer 303, so as to improve the efficiency of hole injection into the electron blocking layer 303 and reduce the driving voltage of the organic electroluminescent device. The hole transport layer 302 may include one type of hole transport material, or may include a plurality of different hole transport materials, which is not particularly limited in the present disclosure. Optionally, the material of the hole transport layer 302 may be a diarylamine compound, a monoarylamine compound, or other types of compounds, and the thickness thereof may be 90-130 nm. Illustratively, in an embodiment of the present disclosure, the material of the hole transport layer 302 is NPB, and the thickness is 100 nm.

Figure 2:
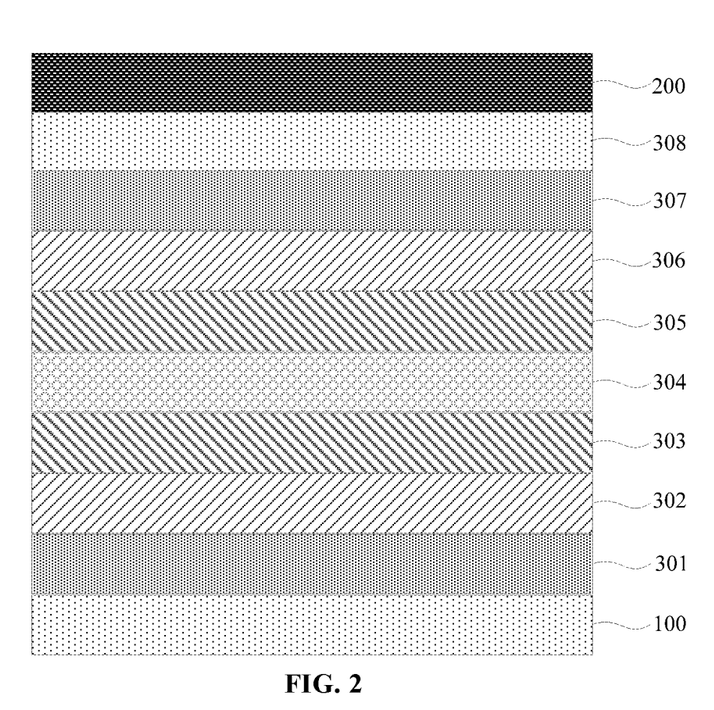
FIG. 2 is a schematic structural diagram of an organic electroluminescent device in an embodiment of the disclosure.

Optionally, referring to FIG. 2, the organic electroluminescent device may further include a hole injection layer 301. The hole injection layer 301 may be located between the hole transport layer 302 and the anode 100, for transporting holes from the anode 100 to the hole transport layer 302 and improving the efficiency of hole injection into the hole transport layer 302. The hole injection layer 301 may include one material or a plurality of different materials, which is not particularly limited in the present disclosure.

Optionally, the electron blocking layer 303 is located between the hole transport layer 302 and the buffer layer 304, and is used to inject holes into the buffer layer 304, and then inject holes into the organic light emitting layer 305. Due to the presence of the buffer layer 304, the holes do not need to directly overcome the large energy barrier between the electron blocking layer 303 and the organic light emitting layer 305, but only need to overcome the small energy barrier between the electron blocking layer 303 and the buffer layer 304, the small energy barrier between the buffer layer 304 and the organic light emitting layer 305. This helps to reduce the driving voltage of the organic electroluminescent device, overcome the insufficient hole mobility of the buffer layer 304 and its adverse impact on the driving voltage. Similarly, this also helps to improve the efficiency of hole injection into the organic light emitting layer 305, and overcomes the insufficient hole mobility of the buffer layer 304 and its adverse effect on the hole injection efficiency.

Optionally, the electron blocking layer 303 has a higher lowest unoccupied molecular orbital (LUMO) energy level, so that the energy level difference between the LUMO energy level of the electron blocking layer 303 and the LUMO energy level of the host material of the organic light emitting layer 305 is relatively large. This in turn makes it possible to block the flow of electrons, prevent the flow of electrons from entering the hole transport layer 302 and causing damage to the hole transport material, and improve the life of the organic electroluminescent device.

Optionally, the electron blocking layer 303 may be selected from: arylamine carbazole-based materials, arylamine furan-based materials, or other types of materials, and its thickness may be 3-20 nm. Exemplarily, in an embodiment of the present disclosure, the material of the electron blocking layer 303 may be TCTA, and the thickness may be 10 nm.

The buffer layer 304 is located between the electron blocking layer 303 and the organic light emitting layer 305, and its thickness may be 1-100 nm. In some embodiments, the thickness of the buffer layer 304 is 0.05 to 0.20 times the thickness of the organic light emitting layer 305. In this way, the performance of the organic electroluminescent device can be improved by thinning the organic light emitting layer 305 of the organic electroluminescent device and adding the buffer layer 304. In other embodiments, the thickness of the buffer layer 304 may be 3-20 nm. Exemplarily, the thickness of the buffer layer 304 is 5 nm.

The organic light emitting layer 305 includes a host material and a guest material mixed with each other, wherein the weight percentage of the guest material is less than the weight percentage of the host material. Holes and electrons recombine in the organic light emitting layer 305 to form excitons, and the host material can transfer the excitons to the guest material, so that the guest material emits fluorescence or phosphorescence.

Optionally, in the organic light emitting layer 305, the weight ratio of the guest material may be from 1% to 8%, so as to prevent the concentration of the guest material from being too large to cause fluorescence quenching. Exemplarily, in an embodiment of the present disclosure, in the organic light emitting layer 305, the weight ratio of the guest material may be 5%.

Optionally, the thickness of the organic light emitting layer 305 may be 20-60 nm. Exemplarily, in an embodiment of the present disclosure, the thickness of the organic light emitting layer 305 may be 40 nm.

Optionally, the host material may be an anthracene-based material. For example, it may be ADN.

Alternatively, the guest material may be a fluorescent material or a phosphorescent material. In an embodiment of the present disclosure, the guest material is a fluorescent material for emitting blue light, and its material can be an arylamine vinyl-based material, an arylamine pyrene-based material, a boron nitrogen-based material, or other types of materials. Exemplarily, in an embodiment of the present disclosure, the guest material may be DSA-Ph.

Optionally, referring to FIG. 2, the organic electroluminescent device may further include a hole blocking layer 306 and an electron transport layer 307. The hole blocking layer 306 is provided on the side of the organic light emitting layer 305 away from the anode 100, and the electron transport layer 307 is provided between the hole blocking layer 306 and the cathode 200.

The hole blocking layer 306 is used to block the diffusion of holes to the electron transport layer 307 and prevent the material of the electron transport layer 307 from being damaged by the holes. The LUMO energy level of the hole blocking layer 306 may also be located between the LUMO energy level of the host material and the LUMO energy level of the electron transport layer 307, in order to improve the efficiency of the electron transport layer 307 in injecting electrons into the organic light emitting layer 305. The material of the hole blocking layer 306 may be triazine-based materials, benzimidazole-based materials, or other types of materials. Exemplarily, in an embodiment of the present disclosure, the material of the hole blocking layer 306 may be TPBi. The thickness of the hole blocking layer 306 may be in the range of 3-20 nm. Exemplarily, in an embodiment of the present disclosure, the thickness of the hole blocking layer 306 may be 10 nm.

The electron transport layer 307 is used to improve the electron injection efficiency of the cathode 200 into the organic light emitting layer 305, and can be selected from: triazine-based materials, cyano-based materials, phenanthroline-based materials, or other types of materials. Exemplarily, in an embodiment of the present disclosure, the material of the electron transport layer 307 may be BPhen. The thickness of the electron transport layer 307 may be in the range of 20-60 nm. Exemplarily, in an embodiment of the present disclosure, the thickness of the electron transport layer 307 may be 40 nm.

Optionally, referring to FIG. 1, the organic electroluminescent device may further include an electron injection layer 308, which is located between the electron transport layer 307 and the cathode 200, and used to improve the efficiency of the cathode 200 in injecting electrons into the electron transport layer 307.

In the following, three different organic electroluminescent devices and the performance test comparison results of the three organic electroluminescent devices are exemplarily provided in order to further explain and describe the structure and performance of the organic electroluminescent device according to the present disclosure.

Device A:

With reference to FIG. 1, the device A includes an anode 100, a hole transport layer 302, an electron blocking layer 303, a buffer layer 304, an organic light emitting layer 305, a hole blocking layer 306, an electron transport layer 307, and a cathode 200 stacked in sequence. The anode 100 has a material of ITO and a thickness of 10 nm. The hole transport layer 302 has a material of NPB and a thickness of 100 nm. The electron blocking layer 303 has a material of TCTA and a thickness of 10 nm. The buffer layer 304 has a material of the compound shown in the third chemical formula, and a thickness of 5 nm. The organic light emitting layer 305 has a thickness of 40 nm, wherein the host material is ADN and the guest material is DAS-Ph. The mass ratio of the guest material in the organic light emitting layer 305 is 5%. The hole blocking layer 306 has a material of TPBi and a thickness of 10 nm. The electron transport layer 307 has a material of BPhen and a thickness of 40 nm. The cathode 200 has a material of magnesium-silver alloy (the mass ratio of magnesium to silver is 9:1), and a thickness of 80 nm.

Device B:

With reference to FIG. 1, the device B includes an anode 100, a hole transport layer 302, an electron blocking layer 303, a buffer layer 304, an organic light emitting layer 305, a hole blocking layer 306, an electron transport layer 307, and a cathode 200 which are sequentially stacked and arranged. The anode 100 has a material of ITO and a thickness of 10 nm. The hole transport layer 302 has a material of NPB and a thickness of 100 nm. The electron blocking layer 303 has a material of TCTA and a thickness of 10 nm. The buffer layer 304 has a material of the compound shown in the fourth chemical formula, and a thickness of 5 nm. The thickness of the organic light emitting layer 305 is 40 nm, wherein the host material is ADN and the guest material is DAS-Ph. The mass ratio of the guest material in the organic light emitting layer 305 is 5%. The hole blocking layer 306 has a material of TPBi, and a thickness of 10 nm. The electron transport layer 307 has a material of BPhen, and a thickness of 40 nm. The cathode 200 has a material of magnesium-silver alloy (the mass ratio of magnesium to silver is 9:1), and a thickness of 80 nm.

Device C:

The device C includes an anode, a hole transport layer, an electron blocking layer, an organic light emitting layer, a hole blocking layer, an electron transport layer, and a cathode that are sequentially stacked. The anode has a material of ITO, and a thickness of 10 nm. The hole transport layer has a material of NPB, and a thickness of 100 nm. The electron blocking layer has a material of TCTA, and a thickness of 10 nm. The thickness of the organic light emitting layer is 45 nm, wherein the host material is ADN and the guest material is DAS-Ph. The mass ratio of the guest material in the organic light emitting layer is 5%. The hole blocking layer has a material of TPBi, and a thickness of 10 nm. The electron transport layer has a material of BPhen, and a thickness of 40 nm. The cathode has a material of magnesium-silver alloy (the mass ratio of magnesium to silver is 9:1), and a thickness of 80 nm.

The structural formula of each compound is as follows:

NPB

TCTA

ADN

DSA-Ph

TPBi

Bphen

In the above-mentioned device A, device B and device C, the material of the buffer layer in device A is the compound shown in the third chemical formula, the material of the buffer layer in device B is the compound shown in the fourth chemical formula, the device C is not provided with a buffer layer, and the thickness of the organic light emitting layer in device C is equal to the sum of the thickness of the buffer layer and the thickness of the organic light emitting layer in device A.

Under the current density of 15 mA/cm$^2$, the driving voltage, luminous efficiency, and T95 lifetime were tested with respect to device A, device B, and device C. The test data of device A and the test data of device B are normalized by taking the test data of device C as 100%. In this way, the test results of device A, device B and device C are obtained, and reference can be made to Table 1.

TABLE 1

Performance Test Results of Devices A, B, and C

| organic electroluminescent device | driving voltage (V) | luminous efficiency (Cd/A) | T95 lifetime (h) |
| --- | --- | --- | --- |
| Device C | 100% | 100% | 100% |
| Device A | 102% | 104% | 117% |
| Device B | 101% | 103% | 115% |

It can be seen from Table 1 that compared to device C, the driving voltage of device A and the driving voltage of device B are significantly improved, and the luminous efficiencies thereof are not reduced. However, the life of the organic electroluminescent device has been significantly improved. This indicates that the organic electroluminescent device provided by the present disclosure can improve the life span of the organic electroluminescent device while maintaining performance such as driving voltage and luminous efficiency.

The present disclosure has also tested the luminous efficiencies (in cd/A) of device A, device B, and device C under different current densities (in mA/cm2). It has been found that, at each current density, the current efficiencies of device A and device B are both higher than that of device C or basically the same as that of device C.

The present disclosure has also tested the brightness changes of each device over time at a current density of 10 mA/cm$^2$. It has been found that as time goes by, the brightness (in nits) of device C decreases significantly higher than those of device A and device B. The brightness of device A and the brightness of device B are basically the same during each time period.

The present disclosure has also tested the current density of each device under different driving voltages. It is found that the starting voltage of each device was basically the same. Under the same driving voltage, the current density of each device was basically the same. The current density of device A was slightly greater than that of the device B. The current density of device B is slightly greater than the current density of device C.

All these tests show that device A and device B are basically the same as device C in terms of luminous efficiency, current efficiency, driving voltage, etc. There is no performance degradation. Device A and device B are significantly better than device C in terms of device life. This shows that compared with an organic electroluminescent device without a buffer layer, the device life of the organic electroluminescent device according to the present disclosure has been significantly improved.

The present disclosure has also tested the distribution of excitons in the organic light emitting layer of device C. According to the test result, in the organic light emitting layer, the concentration of excitons is greater on the side closer to the electron blocking layer, and the concentration of excitons is smaller on the side closer to the hole blocking layer. It can be seen that in device C, electrons and holes are mainly recombined on the side closer to the electron blocking layer, and electrons easily enter the electron blocking layer to damage the electron blocking layer. In device A and device B, because the efficiency of injecting holes into the organic light emitting layer is improved, the recombination rate of electrons is increased, and the electrons entering the electron blocking layer and the buffer layer are reduced. In addition, the material of the buffer layer has an excellent electron tolerance, which can effectively withstand electrons and use holes to recombine with the incoming electrons, further reducing the electrons entering the electron blocking layer. Therefore, the organic electroluminescent device of the present disclosure can effectively reduce the impact and damage of electrons to the electron blocking layer, and improve the life of the organic electroluminescent device.

An embodiment of the present disclosure also provides a display panel, which includes any one of the organic electroluminescent devices described in the foregoing organic electroluminescent device embodiments. The display panel can be a mobile phone screen, a computer screen, a smart watch screen, or other types of display panels. Since the display panel has any one of the organic electroluminescent devices described in the above-mentioned organic electroluminescent device embodiments, it has the same beneficial effects, and the present disclosure will not be repeated here.

An embodiment of the present disclosure also provides a display device, which includes any one of the display panel embodiments described above. The display device can be a television, a notebook computer, a smart phone, or other types of display devices. Since the display device has any one of the display panels described in the above display panel embodiments, it has the same beneficial effects, which will not be repeated in the present disclosure.

An embodiment of the present disclosure also provides a light emitting device, which includes any one of the organic electroluminescent devices described in the above-mentioned embodiments. The light emitting device may be a lighting lamp, a warning light, or other types of light emitting devices. Since the light emitting device has any one of the organic electroluminescent devices described in the above-mentioned organic electroluminescent device embodiments, it has the same beneficial effects, and the present disclosure will not be repeated here.

Those skilled in the art will easily think of other embodiments of the present disclosure after considering the specification and practicing the content disclosed herein. The present application is intended to cover any variations, uses, or adaptive changes of the present disclosure. These variations, uses, or adaptive changes follow the general principle of the present disclosure and include common knowledge or conventional technical means in the technical field that are not disclosed in the present disclosure. The description and the embodiments are only regarded as exemplary, and the true scope and spirit of the present disclosure are limited by the appended claims.

The invention claimed is:

1. An organic electroluminescence device, comprising:
   an anode, an electron blocking layer, a buffer layer, an organic light emitting layer, and a cathode which are stacked in sequence, wherein:
   a thickness of the buffer layer is in a range from 1 nm to 100 nm;
   a material of the buffer layer comprises a compound shown in a first chemical formula which is as follows:

X is O or S; one of Y and Z is N($R_4$) and the other of Y and Z is a single bond;

$R_1$, $R_2$, and $R_3$ are each independently selected from: hydrogen, deuterium, fluorine, cyano, halogen, alkyl group with 1 to 6 carbon atoms, cycloalkyl group with 5 to 10 carbon atoms, substituted or unsubstituted aryl group with 6 to 30 carbon atoms in total, and substituted or unsubstituted heteroaryl group with 4 to 30 carbon atoms in total;

at least one of $R_1$, $R_2$, and $R_3$ is selected from a group shown in a second chemical formula which is as below:

and $R_4$ is selected from: alkyl group with 1 to 6 carbon atoms, cycloalkyl group with 5 to 10 carbon atoms, aryl group with 6 to 30 carbon atoms, and heteroaryl group with 4 to 30 carbon atoms.

2. The organic electroluminescent device according to claim 1, wherein
$R_1$, $R_2$ and $R_3$ are each independently selected from: hydrogen, and substituted or unsubstituted group Ar, wherein
the unsubstituted group Ar is selected from groups which are as follows:

and the substituted group Ar is a new group formed by substituting the unsubstituted group Ar with one or more substituent groups, wherein each substituent group on the substituted group Ar is independently selected from: deuterium, fluorine, chlorine, cyano, alkyl group with 1 to 6 carbon atoms, and cycloalkyl group with 3 to 10 carbon atoms; and in a case that the substituted group Ar has more than one substituent group, each substituent group is the same or different.

3. The organic electroluminescence device according to claim 1, wherein the buffer layer comprises one or both of:
a compound represented by a third chemical formula which is as below:

and
a compound represented by a fourth chemical formula which is as below

4. The organic electroluminescence device according to claim 1, wherein the organic light emitting layer is configured to emit blue light.

5. The organic electroluminescent device according to claim 1, wherein the thickness of the buffer layer is 0.05 to 0.20 times a thickness of the organic light emitting layer.

6. The organic electroluminescence device according to claim 1, wherein:
the organic light emitting layer comprises a host material and a guest material mixed with each other; and
a lowest unoccupied molecular orbital energy level of the host material is lower than a lowest unoccupied molecular orbital energy level of the material of the buffer layer by at least 0.15 eV.

7. The organic electroluminescence device according to claim 6, wherein the lowest unoccupied molecular orbital energy level of the host material is in a range from −2.75 eV to −3.15 eV.

8. The organic electroluminescence device according to claim 6, wherein the lowest unoccupied molecular orbital energy level of the material of the buffer layer is in a range from −2.25 eV to −2.65 eV.

9. The organic electroluminescence device according to claim 6, wherein
a highest occupied molecular orbital energy level of the material of the buffer layer is higher than a highest occupied molecular orbital energy level of the host material, and the highest occupied molecular orbital energy level of the material of the buffer layer is in a range from −5.4 eV to −6 eV.

10. The organic electroluminescence device according to claim 9, wherein the highest occupied molecular orbital energy level of the material of the buffer layer is in a range from −5.5 eV to −5.8 eV.

11. The organic electroluminescence device according to claim 9, wherein the highest occupied molecular orbital energy level of the host material is in a range from −5.8 eV to −6.2 eV.

12. The organic electroluminescence device according to claim 9, wherein a highest occupied molecular orbital energy level of a material of the electron blocking layer is in a range from −5.25 eV to −5.65 eV, and is higher than the highest occupied molecular orbital energy level of the material of the buffer layer.

13. The organic electroluminescent device according to claim 6, wherein a hole mobility of the host material is less than an electron mobility of the host material.

14. The organic electroluminescence device according to claim 6, wherein
an excited triplet energy level of the material of the buffer layer is not less than 2.5 eV; and
the host material is a thermally activated delayed fluorescent material.

15. The organic electroluminescence device according to claim 1, wherein the material of the buffer layer is composed of a compound represented by the first chemical formula.

16. The organic electroluminescence device according to claim 1, wherein the thickness of the buffer layer is in a range from 3 nm to 20 nm.

17. A display panel, comprising:
an organic electroluminescent device comprising an anode, an electron blocking layer, a buffer layer, an organic light emitting layer, and a cathode which are stacked in sequence, wherein:
a thickness of the buffer layer is in a range from 1 nm to 100 nm;
a material of the buffer layer comprises a compound shown in a first chemical formula which is as follows:

X is O or S; one of Y and Z is N($R_4$) and the other of Y and Z is a single bond;
$R_1$, $R_2$, and $R_3$ are each independently selected from: hydrogen, deuterium, fluorine, cyano, halogen, alkyl group with 1 to 6 carbon atoms, cycloalkyl group with 5 to 10 carbon atoms, substituted or unsubstituted aryl group with 6 to 30 carbon atoms in total, and substituted or unsubstituted heteroaryl group with 4 to 30 carbon atoms in total;
at least one of $R_1$, $R_2$, and $R_3$ is selected from a group shown in a second chemical formula which is as below:

and
$R_4$ is selected from: alkyl group with 1 to 6 carbon atoms, cycloalkyl group with 5 to 10 carbon atoms, aryl group with 6 to 30 carbon atoms, and heteroaryl group with 4 to 30 carbon atom.

18. A display device, comprising:
a display panel comprising an organic electroluminescent device, the organic electroluminescent device comprising an anode, an electron blocking layer, a buffer layer, an organic light emitting layer, and a cathode which are stacked in sequence, wherein:
a thickness of the buffer layer is in a range from 1 nm to 100 nm;
a material of the buffer layer comprises a compound shown in a first chemical formula which is as follows:

X is O or S; one of Y and Z is N($R_4$) and the other of Y and Z is a single bond;
$R_1$, $R_2$, and $R_3$ are each independently selected from: hydrogen, deuterium, fluorine, cyano, halogen, alkyl group with 1 to 6 carbon atoms, cycloalkyl group with 5 to 10 carbon atoms, substituted or unsubstituted aryl group with 6 to 30 carbon atoms in total, and substituted or unsubstituted heteroaryl group with 4 to 30 carbon atoms in total;
at least one of $R_1$, $R_2$, and $R_3$ is selected from a group shown in a second chemical formula which is as below:

and
$R_4$ is selected from: alkyl group with 1 to 6 carbon atoms, cycloalkyl group with 5 to 10 carbon atoms, aryl group with 6 to 30 carbon atoms, and heteroaryl group with 4 to 30 carbon atoms.

* * * * *